US009173679B2

(12) United States Patent
Tzachar et al.

(10) Patent No.: US 9,173,679 B2
(45) Date of Patent: Nov. 3, 2015

(54) INTRAOSSEOUS DEVICE FOR INSERTING A CANNULA INTO A BONE

(75) Inventors: Barak Tzachar, Petach Tikva (IL); Alexander Kalnitskiy, Maale Adumim (IL); Yosef Gomberg, Psagot (IL)

(73) Assignee: Waismed Ltd., Herzliya (IL)

( * ) Notice: Subject to any disclaimer, the term of this patent is extended or adjusted under 35 U.S.C. 154(b) by 172 days.

(21) Appl. No.: 14/009,937

(22) PCT Filed: Apr. 2, 2012

(86) PCT No.: PCT/IL2012/000141
§ 371 (c)(1),
(2), (4) Date: Oct. 4, 2013

(87) PCT Pub. No.: WO2012/140645
PCT Pub. Date: Oct. 18, 2012

(65) Prior Publication Data
US 2014/0046327 A1 Feb. 13, 2014

(30) Foreign Application Priority Data
Apr. 11, 2011 (IL) .......................................... 212263

(51) Int. Cl.
*A61B 17/34* (2006.01)
*A61B 10/02* (2006.01)
*A61M 5/20* (2006.01)

(52) U.S. Cl.
CPC ........... *A61B 17/3472* (2013.01); *A61B 10/025* (2013.01); *A61B 17/34* (2013.01); *A61B 17/3415* (2013.01); *A61B 17/3494* (2013.01); *A61B 2010/0258* (2013.01); *A61B 2017/348* (2013.01); *A61B 2017/3492* (2013.01); *A61M 2005/208* (2013.01)

(58) Field of Classification Search
CPC ..................... A61B 10/025; A61B 2010/0258; A61B 17/34; A61B 17/3415; A61B 17/3472; A61B 2017/348; A61B 2017/3492; A61B 17/3494; A61B 5/1433; A61B 5/1444; A61B 5/15113; A61B 17/32053; A61M 2005/206; A61M 2005/2073; A61M 2005/208
See application file for complete search history.

(56) References Cited

U.S. PATENT DOCUMENTS

| 8,287,467 B2 * | 10/2012 | List et al. ...................... 600/583 |
| 2003/0225344 A1 | 12/2003 | Miller |
| 2003/0225411 A1 | 12/2003 | Miller |
| 2004/0220497 A1 | 11/2004 | Findlay et al. |
| 2005/0033235 A1 | 2/2005 | Flint |

(Continued)

FOREIGN PATENT DOCUMENTS

WO    WO2008/065646    6/2008

OTHER PUBLICATIONS

Supplementary European Search Report dated Oct. 7, 2014; European Application No. EP12770984; 5 pages.

(Continued)

*Primary Examiner* — Larry E Waggle, Jr.
(74) *Attorney, Agent, or Firm* — Blank Rome LLP

(57) ABSTRACT

The invention relates to a device for the insertion of a cannula into a bone of a patient, which comprises: (a) an activator assembly for activating the device; (b) needle assembly which comprises a stylet and cannula; (c) barrel assembly for containing said stylet and cannula in a loaded state prior to the device activation; and (d) a setting assembly for adjusting the penetration depth of said cannula into the patient's bone.

15 Claims, 16 Drawing Sheets

(56) References Cited

U.S. PATENT DOCUMENTS

| | | |
|---|---|---|
| 2005/0171504 A1 | 8/2005 | Miller |
| 2006/0015066 A1 | 1/2006 | Turieo et al. |
| 2006/0052790 A1 | 3/2006 | Miller |
| 2008/0208136 A1 | 8/2008 | Findlay et al. |
| 2009/0124979 A1 | 5/2009 | Raymond et al. |
| 2010/0137740 A1 | 6/2010 | Miller |
| 2010/0152616 A1 | 6/2010 | Beyhan et al. |
| 2010/0152665 A1 | 6/2010 | Hasted |
| 2010/0160867 A1 | 6/2010 | Miller et al. |
| 2010/0160868 A1 | 6/2010 | Miller et al. |
| 2010/0217105 A1 | 8/2010 | Yodfat et al. |
| 2010/0298831 A1 | 11/2010 | Browne et al. |
| 2010/0312246 A1 | 12/2010 | Browne et al. |

OTHER PUBLICATIONS

International Search Report; Dated: Aug. 27, 2012; International Application No. PCT/IL2012/000141; International Filing Date: Apr. 2, 2012; 2 pages.

\* cited by examiner

Detail A

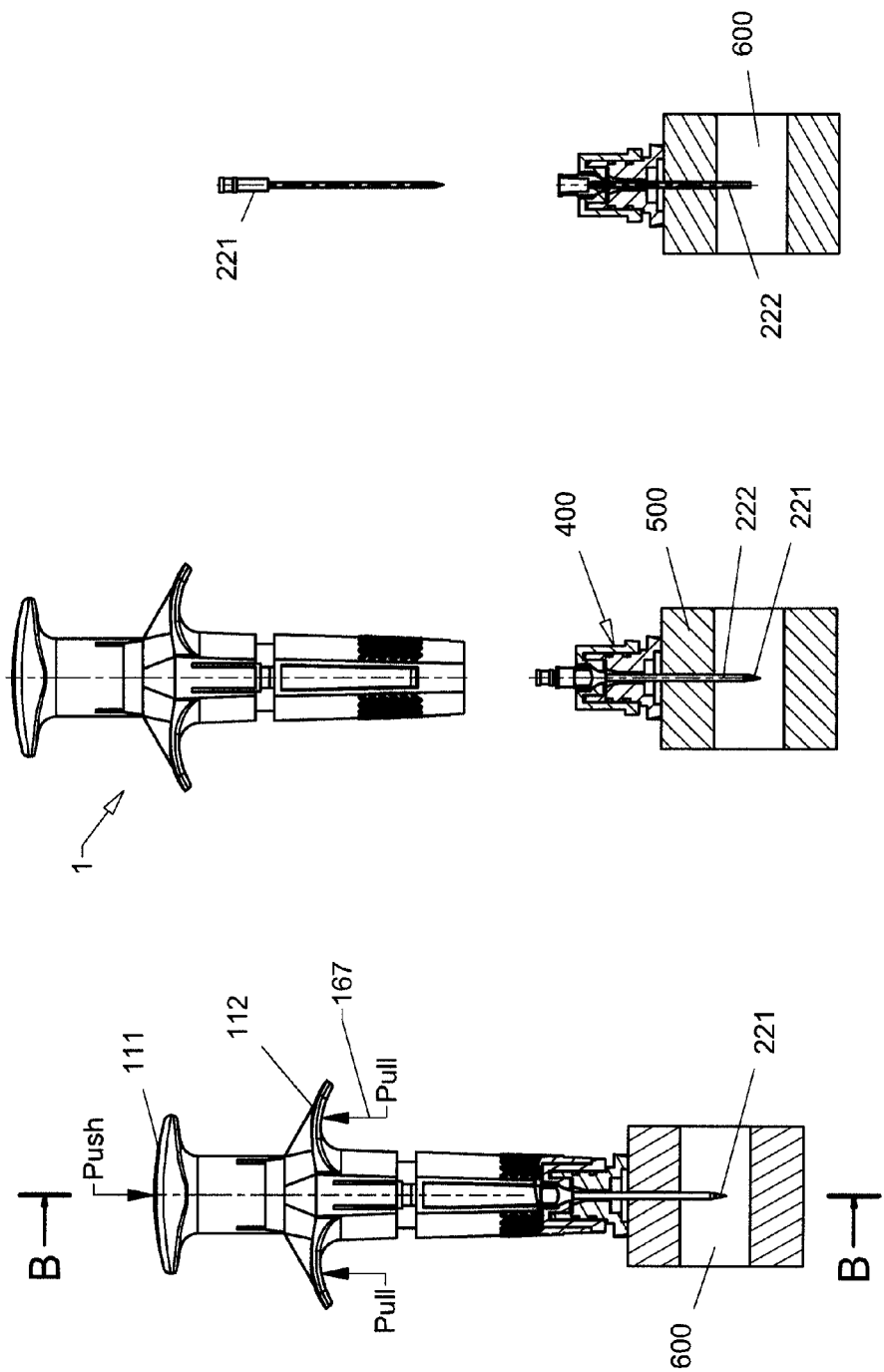

INTRAOSSEOUS DEVICE FOR INSERTING A CANNULA INTO A BONE

FIELD OF THE INVENTION

The present disclosure relates to instruments for the insertion of a cannula-stylet into the marrow of a bone, for the purpose of administration of drugs fluids and blood or for aspirating samples of bone marrow through said cannula. More specifically, the invention relates to such a device that comprises more safety means than prior art devices, and which provides a better support for the cannula over the patient's body after the activation of the device.

BACKGROUND OF THE INVENTION

Intraosseous injection devices (IID) for causing a cannula and at least a portion of stylet (hereinafter the pair of cannula and stylet are also referred to as "trocar needle") to penetrate into a bone are well known in the art. Such devices are typically used in life saving cases where the injection of drugs to the blood circuitry is required, while it is difficult for the medical staff to locate the patient's vein within a reasonable time. This device is also used for the extraction of a sample from a patient's bone marrow.

US 2010/0160868, US 2003/0225344, US 2010/0298831, US 2008/0208136, US 2006/0015066, US 2010/0160867, US 2010/0152616, US 2010/0137740, US 2006/0052790, US 2005/0171504, US 2003/0225411, and US 2010/0312246, all describe some sorts of intraosseous devices.

It has been found, however, that such devices suffer from safety problems and from improper of operation problems. For example, there are known cases in which the doctor has activated the device in the opposite direction, causing a portion of the trocar needle to penetrate the doctor's body instead of the patient's body. In other cases, devices have been early activated, before positioning the device at the exact point over the patient's body.

Furthermore, prior art devices do not provide a very stable support to the cannula, after causing its penetration into the patient's bone.

All the above drawbacks endanger both the patient's life and the device operator, as they involve injury to the operator, loss of the whole device or components thereof (most of such devices are designed for one-time use, and the operator may not have a spare device), or a loss of precious time. Moreover, even if the trocar needle has successfully inserted into the bone, the administration of the drugs into the bone may not succeed due to instability of the cannula, after the penetration operation.

It is therefore an object of the present invention to provide an intraosseous device which is safer both to the operator and to the patient. More specifically it is an object of the invention to provide a device whose various known types of erroneous operation are eliminated, or at least minimized.

It is another object of the present invention to provide a device which is more reliable in operation.

It is still another object of the present invention to provide a device provides support to the cannula over the patient's body, after activation and disconnection of the device from the cannula.

Other objects and advantages of the invention will become apparent as the description proceeds.

SUMMARY OF THE INVENTION

The invention relates to a device for the insertion of a cannula into a bone of a patient, which comprises: (a). an activator assembly for activating the device; (b). needle assembly which comprises a stylet and cannula; (c). barrel assembly for containing said stylet and cannula in a loaded state prior to the device activation; and (d). a setting assembly for adjusting the penetration depth of said cannula into the patient's bone; wherein: (e). said activator assembly comprises a first safety mechanism in a form of a safety catch that prevents activation of the device unless said safety catch is released; (f). said activator assembly comprises a trigger that triggers activation of the device only if pulled toward a proximal direction, while pulling to the distal direction is prevented, thereby eliminating reverse direction activation; (g). the device comprises a second safety mechanism that prevents activation of the device by locking it unless said setting assembly is pushed against the patient's body, thereby causing closure of a gap in the device between a jacket which is located in said barrel assembly and said activator assembly, hence the device becomes ready for activation only when placed properly against the patient's body.

Preferably, said gap between said barrel assembly and said activator assembly is formed by means of a secondary spring which is located between said two assemblies.

Preferably, when the device is pushed against the patient's body, but released without triggering, the gap is recreated, and the device becomes locked again.

Preferably, said needle assembly is maintained in a loaded state within the device by means of a loaded main spring.

Preferably, said setting assembly automatically separate from the main body of the device together with said needle assembly after activation of the device, and said setting assembly remains on the patient's body to support, stabilize, fix and maintain the cannula in place.

Preferably, the stylet is removed from the cannula after activation of the device, leaving the cannula penetrated within the bone, thereby producing a channel from the exterior of the patient's body to within the medullary cavity of the bone.

Preferably, said first safety mechanism is released by means of rotating relative to the rest of the device.

Preferably, said stylet is maintained within said cannula, before activation of the device.

Preferably, said setting assembly comprises a turning element with a thread, which defines the depth of penetration by means of rotation.

Preferably, said needle assembly is pushed toward the bone upon activation of the device by means of a hammer.

Preferably, said needle assembly further comprises a first holder, said first holder releases the stylet and cannula after the triggering of the device.

Preferably, said first holder automatically releases the setting assembly after the triggering of the device and insertion of said stylet and cannula into the bone.

Preferably, said needle assembly comprises a needle holder that holds the needle aligned in place during the loaded state of the device.

Preferably, said second safety mechanism allows activation of the device only when positioned essentially perpendicular to the bone surface.

Optionally, the setting assembly is pre-adjusted to a fixed penetration depth (i.e., a pre-adjustment by the manufacturer to a specific depth that does not enable the user making any further adjustment).

BRIEF DESCRIPTION OF THE DRAWINGS

In the drawings:

FIG. 17d shows the device just after its activation;

FIG. 17e shows the device of the invention after separation of the main body from the setting assembly;

FIG. 17f shows the removal of the stylet from within the cannula, after the completion of the penetration;

DETAILED DESCRIPTION OF PREFERRED EMBODIMENTS

The present invention relates to an intraosseous injection device (IID). The IID of the invention enables introduction of fluid into the bone marrow. As will be elaborated hereinafter, the device of the present invention provides a cannula into the bone marrow. Thereafter, the fluid can be provided through said cannula to within the bone marrow. The IID of the invention is typically used in emergency cases, where injection into the bone marrow provides the fastest effect. Moreover, the device can be used in cases when there is a need to obtain a sample from the bone marrow, for diagnosis purposes.

The IID is essentially a spring loaded device, that upon activation "shoots" a portion of the needle assembly by the force generated by the spring's expansion, causing a stylet and cannula of the needle assembly to penetrate into the bone. As will be shown in detail, the device comprises two safety measures for preventing erroneous or accidental operation. The first safety measure of the IID requires the user to make a 90° turn of a safety catch, and the second safety measure requires the user to apply a linear force directed against the patient's body. Only after the release of said two safety measures, the device is operable. In such a manner, erroneous or accidental operations, which happened from time to time, are prevented. More specifically, the safety measures enable the stylet and cannula of the needle assembly to be applied only toward the bone, and not in the opposite direction, as happened in prior art devices.

Figure 1:
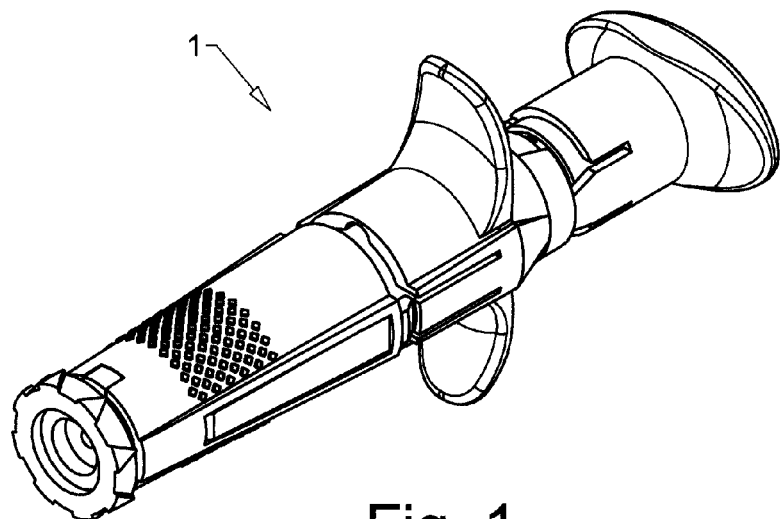
FIG. 1 shows the general structure of the IID device of the present invention.
Figure 2:
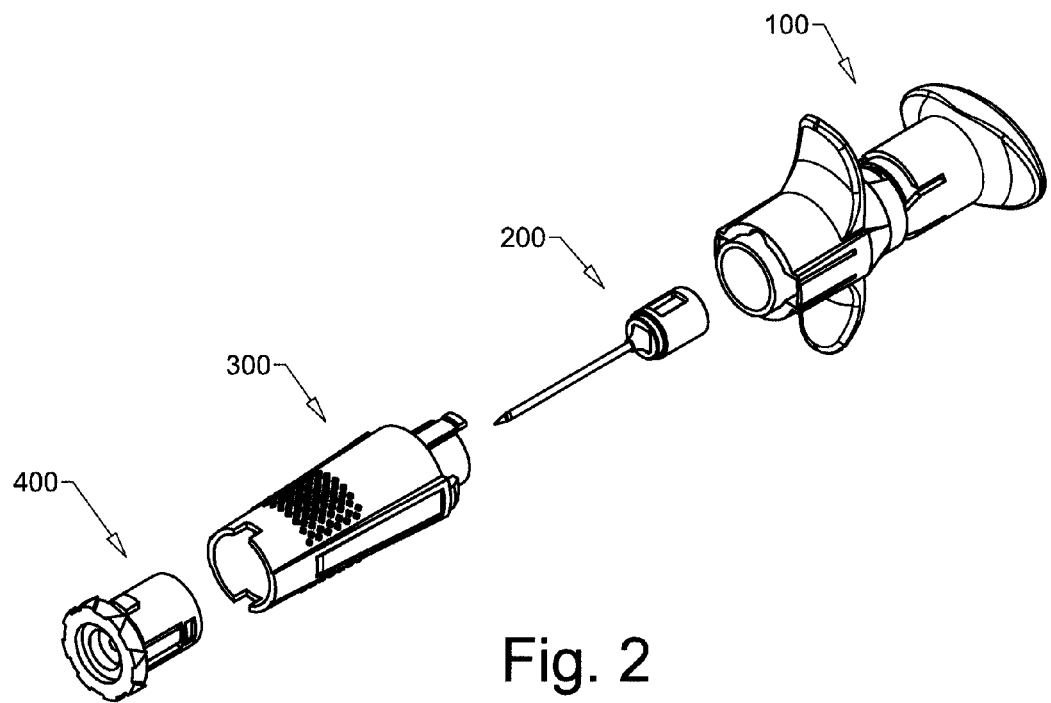
FIG. 2 illustrates the four main assemblies of the IID device of the present invention.

FIG. 1 shows the IID 1 of the present invention, while FIG. 2 shows the various assemblies of the IID 1. In general, IID 1 comprises four assemblies, as follows: Activator assembly 100, needle assembly 200, barrel assembly 300, and setting assembly 400.

The activator assembly 100, which is shown in FIGS. 3, 4, 5, and 6 is used for activating the device. It comprises: (a) first safety catch 111, for releasing the device from a locked state into an operable state; (b) trigger 112 for triggering the device; (c) first tube 113; (d) main spring 114, (e) hammer 115; and (f) two balls 116a and 116b.

The needle assembly 200, which is shown in FIGS. 12, 13, 17f, and 21, comprises: (a) stylet 221 (best seen in FIG. 21); (b) cannula 222; and (c) first holder 223. The first holder 223 comprises snaps 224a and 224b for holding the cannula 222. The stylet 221 is typically located within cannula 222, and upon activation of the device, these two elements together penetrate the patient's body towards the bone. The first holder 223 remains within the device even after its activation. Moreover, said first holder also holds the needle aligned in place during the loaded state of the device.

Figure 7:
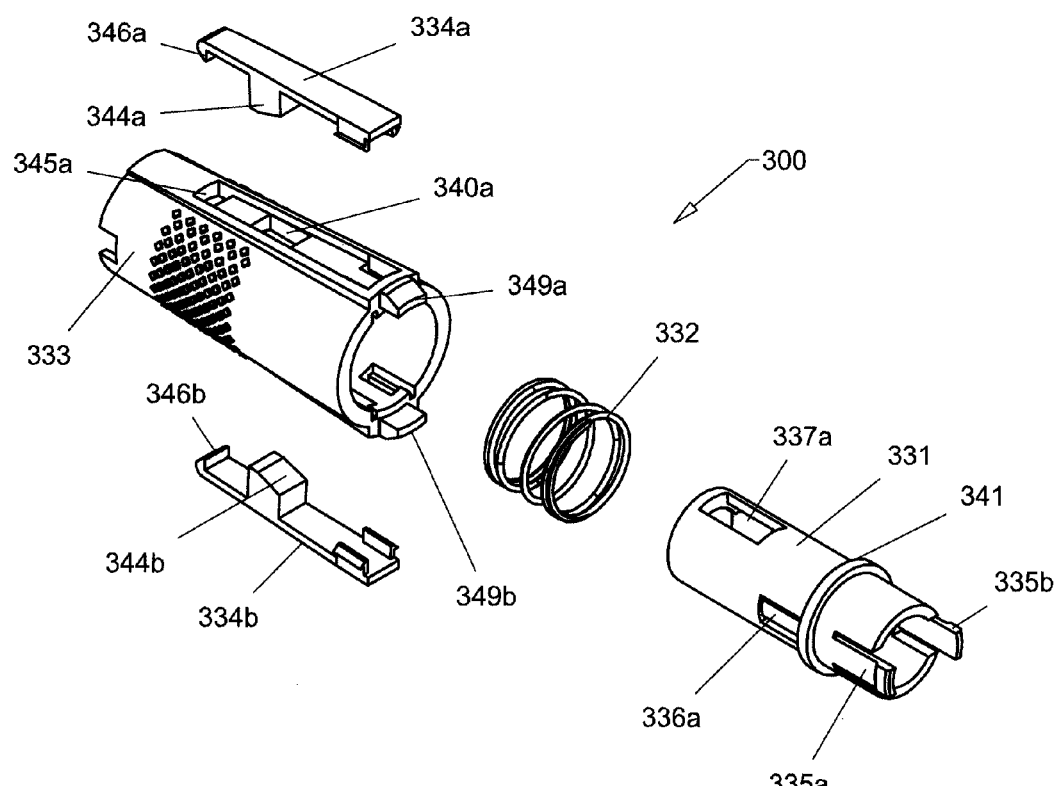
FIG. 7 shows an exploded view of the barrel assembly.
Figure 8:
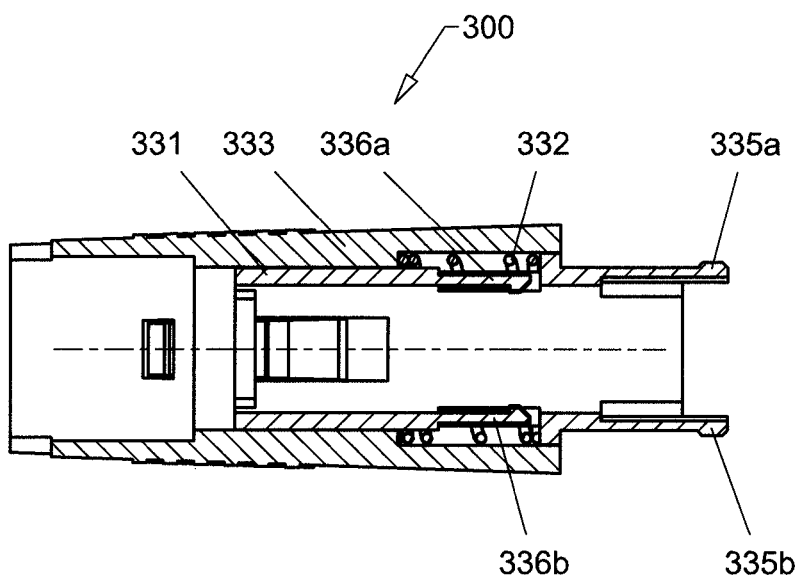
FIG. 8 is a cross sectional front view of the barrel assembly.
Figure 9:
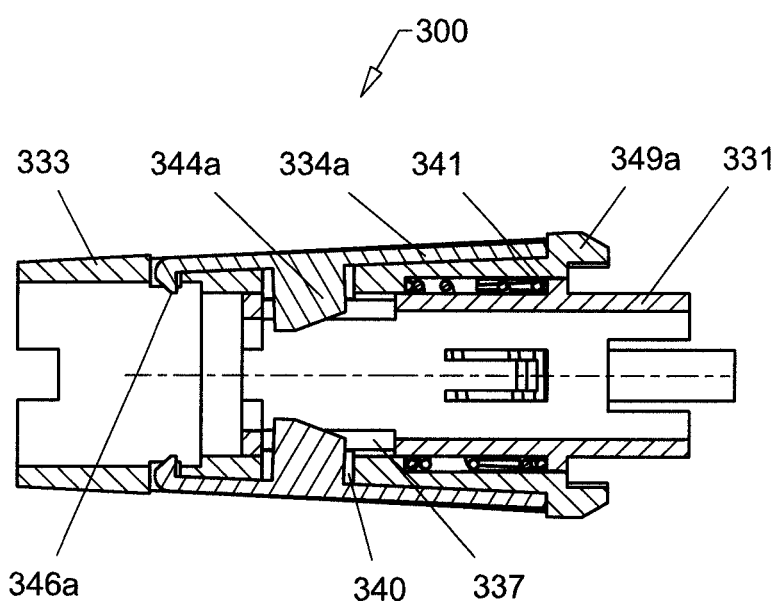
FIG. 9 is a cross sectional top view of the barrel assembly.

The barrel assembly 300, which is shown in FIGS. 7, 8, and 9 is used for directing the trocar needle toward the body, for releasing the second safety catch, and releasing, upon activation of the device, of the setting assembly 400, stylet 221 and cannula 222 toward the body. The barrel assembly 300 comprises: (a) second tube 331; (b) secondary spring 332; (c) barrel jacket 333; and (d) two elastic latches 334a and 334b.

Figure 10:
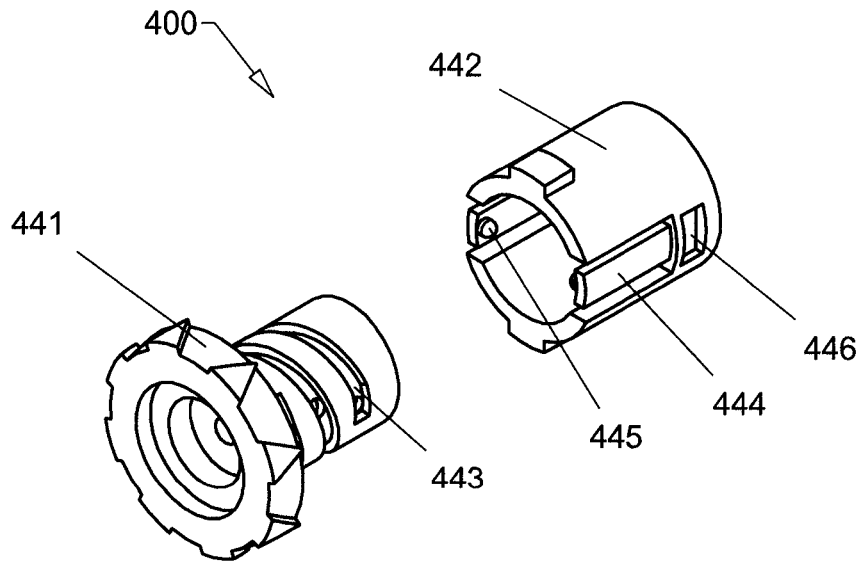
FIG. 10 shows an exploded view of the setting assembly.
Figure 11:
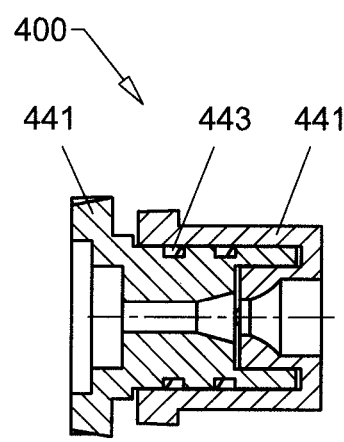
FIG. 11 is a cross sectional view of the setting assembly.
Figure 12:
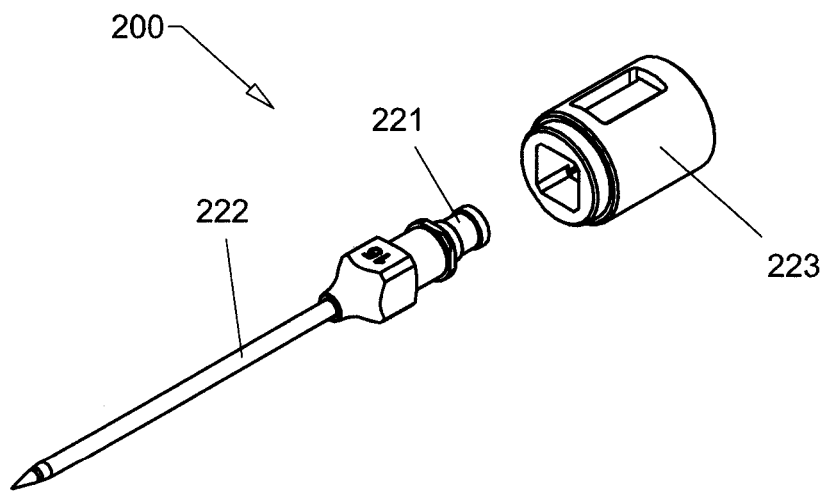
FIG. 12 shows an exploded view of the needle assembly.
Figure 13:
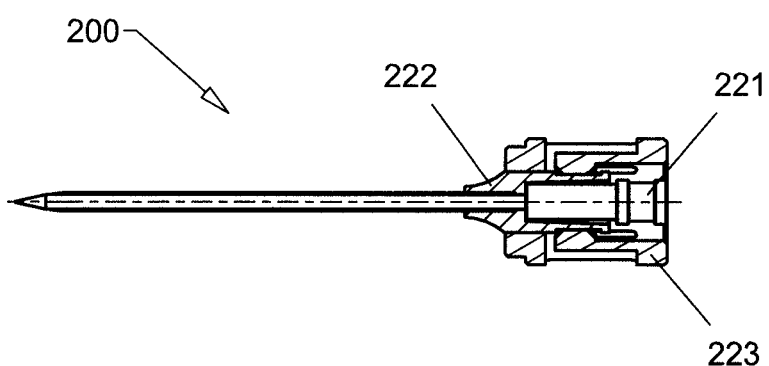
FIG. 13 is a cross sectional view of the needle assembly.
Figure 14:
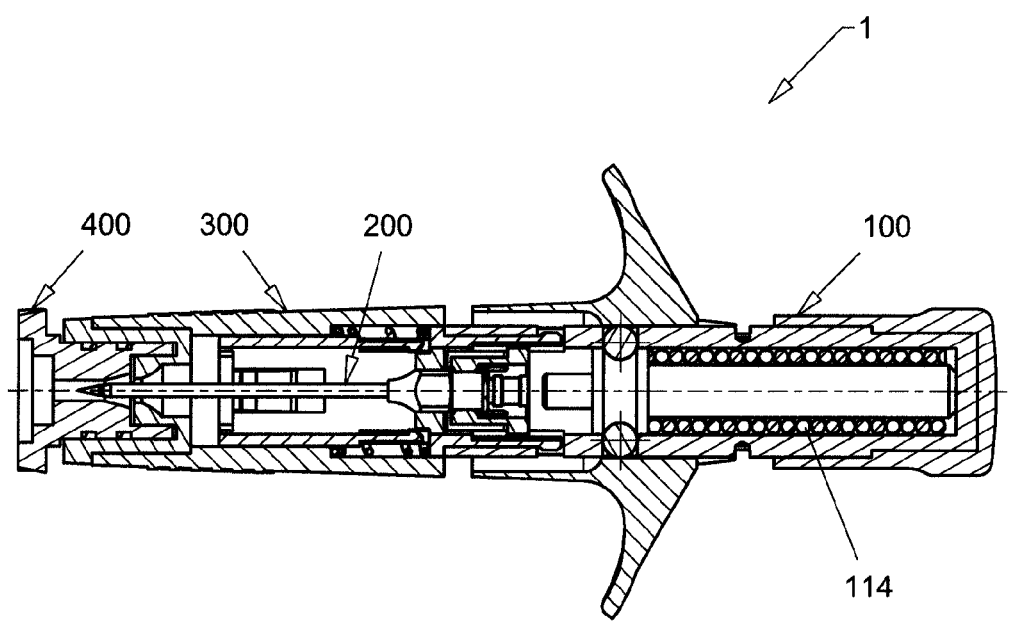
FIG. 14 is a cross sectional front view of the device of the invention in its cocked state.

The setting assembly 400 which is shown in FIGS. 10 and 11 is used for tuning the depth of the penetration. Moreover, after the activation of the device, the setting assembly 400 is released from the main body of the device 1, together with the cannula 222 and stylet 221, and it maintains the cannula and stylet in a stable state on the patient's body. The setting assembly 400 comprises: (a) tuning element 441; and (b) second holder 442.

The various operation stages of the device are illustrated in FIGS. 17a-17f. The body of the patient is indicated by numeral 500. The initial stage of the device is shown in FIGS. 17a, 14, 15, and 16. In the initial stage, the device 1 is cocked and locked. More specifically, the cocked configuration is provided when the needle assembly 200 is fully positioned within the device 1, and the main spring 114 of the activator assembly 100 is loaded. During the locked configuration, the safety catch 111 is in its "locked" position (see also FIG. 6a). Moreover, a gap 160 exists between trigger 112 and barrel jacket 333. As will be elaborated, the gap provides a second safety means, as the device cannot be activated as long as this gap exists, even when safety catch 111 is turned into its "unlock" state (best shown in FIG. 6b).

Before the use of the device, the penetration depth may be tuned. The tuning selects between several penetration depths, and is performed by turning the turning element 441 to a selected angular position.

Figure 17C:
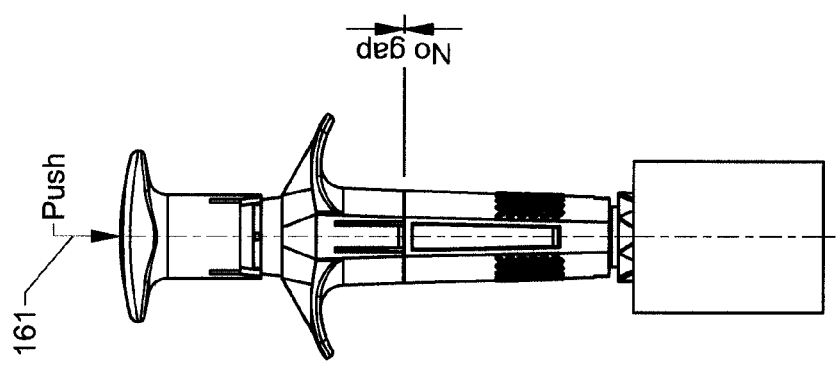
FIG. 17c shows the device of the invention just before its activation.
Figure 17B:
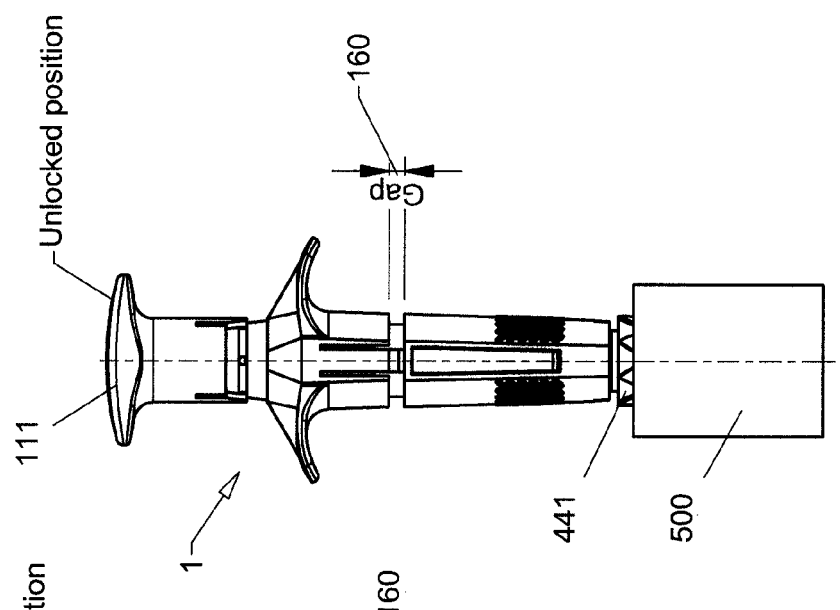
FIG. 17b shows the device of the invention in its unlocked state as provided by turning the safety catch into its unlocked position.
Figure 17A:
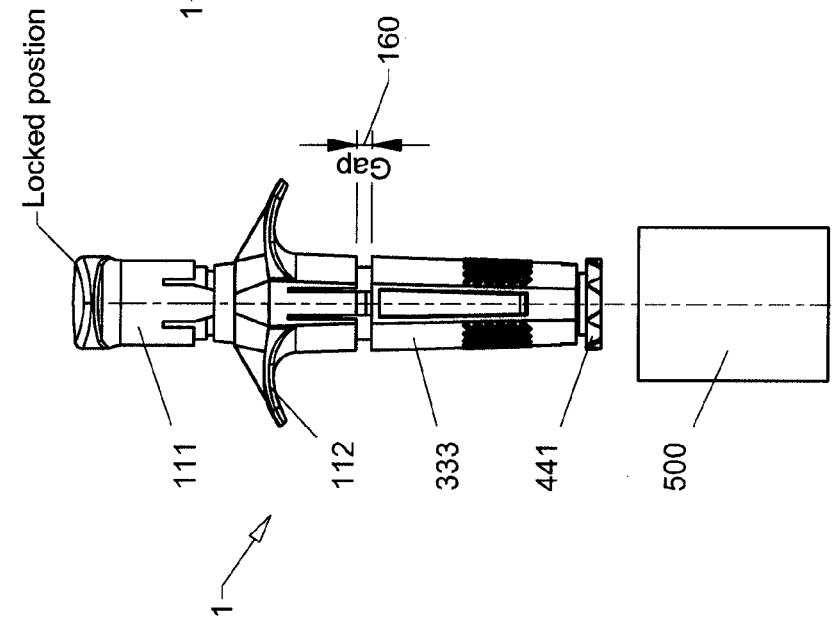
FIG. 17a shows the device of the invention in its initial stage.
Figure 18:
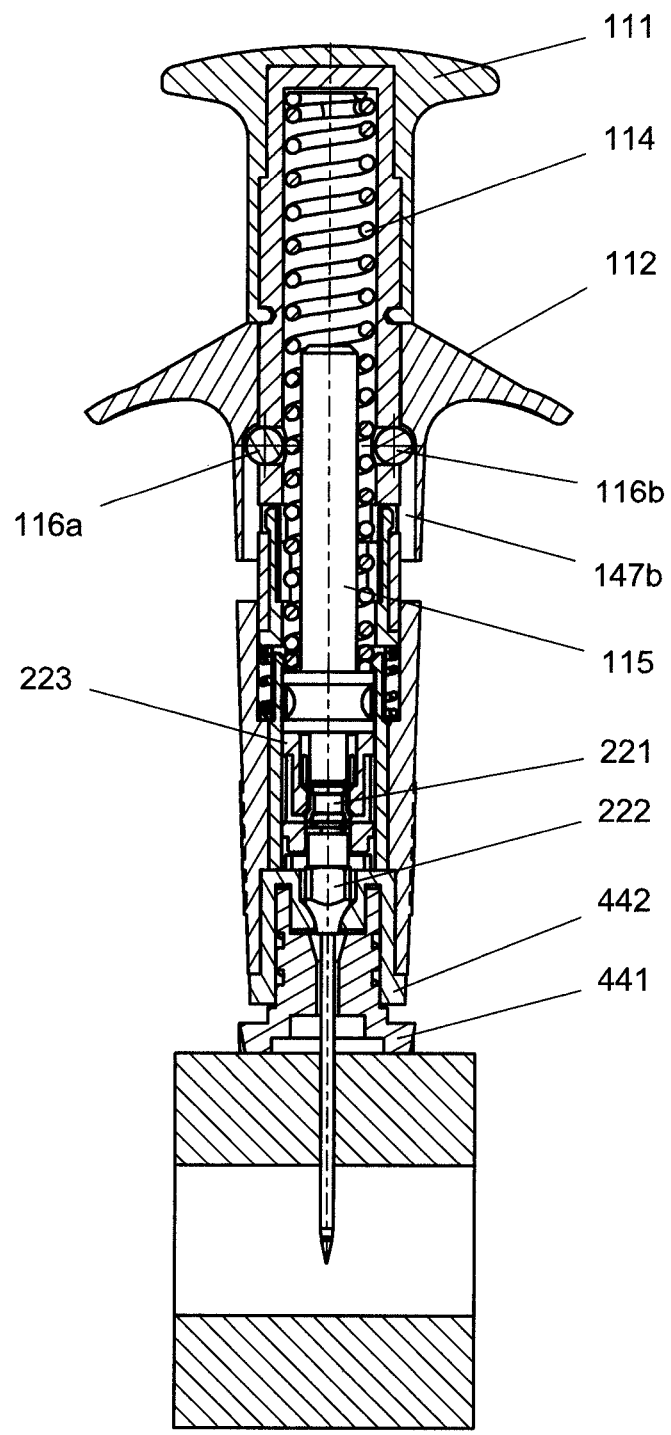
FIG. 18 is a front cross sectional view FIG. 17d, showing the device just after its activation.
Figure 19:
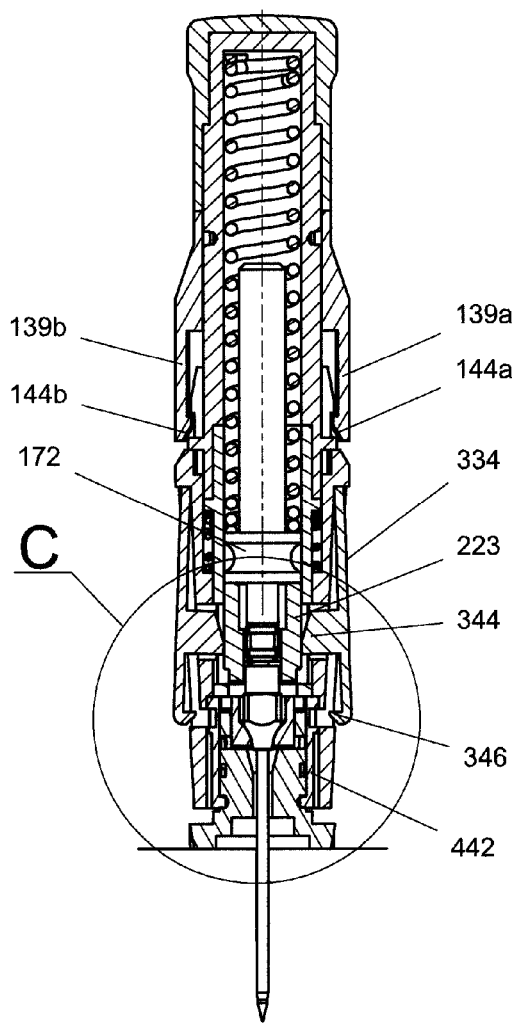
FIG. 19 is a cross sectional view made along cutting plane B-B of FIG. 17d.
Figure 20:
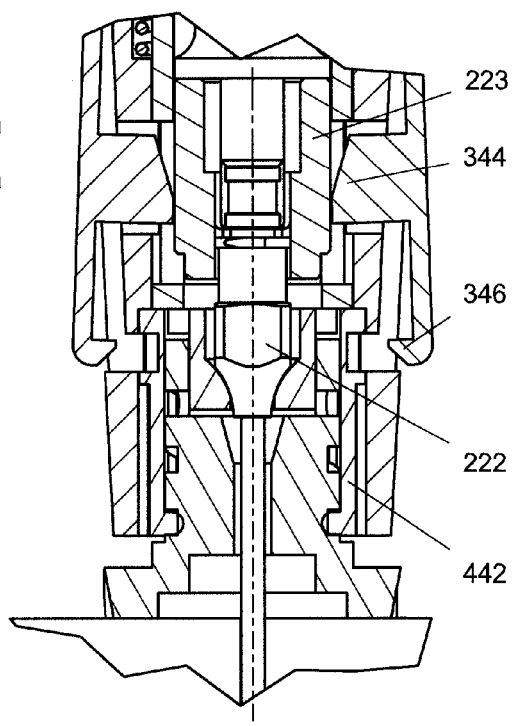
FIG. 20 is a detailed view of section C of FIG. 19.
Figure 21:
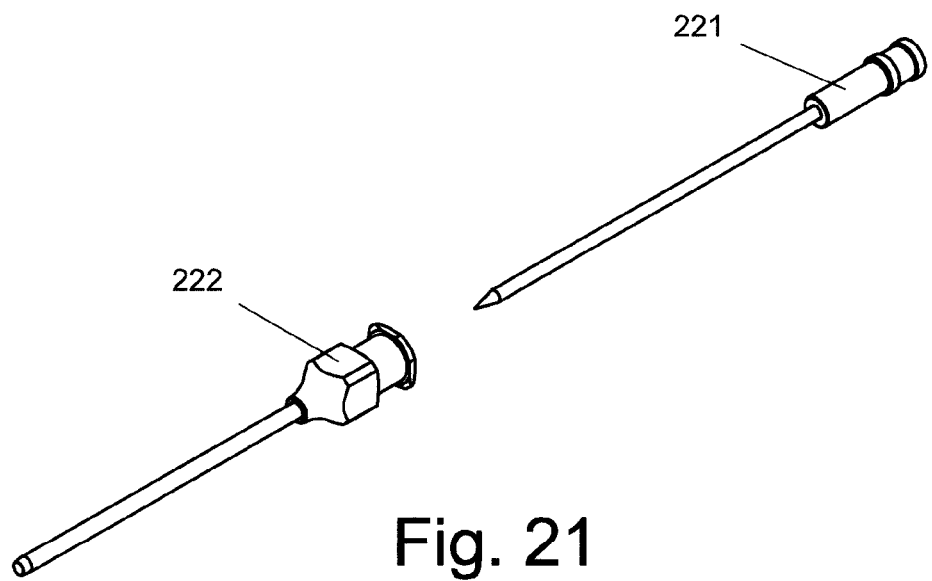
FIG. 21 shows the stylet and cannula of the device.

FIG. 17b shows the device in its unlocked state as provided by turning the safety catch 111 (first safety means) into its unlocked position (i.e., turning it 90° from its initial locked position). The device 1 is in contact with the patient's body 500, however, it is still inoperable, as the gap 160 still exists.

FIG. 17c shows the state of the device 1 just before its activation. More specifically, the second safety means is neutralized (in a manner which will be elaborated hereinafter) by the user applying a linear force 161 on the safety catch 111 directed to the patient's body 500, thereby eliminating gap 160.

FIGS. 17d, 18, 19, and 20 show the device 1 just after its activation. The activation is provided by pulling trigger 112 in a proximal direction 167, i.e., away from patient's body 500. The activation of the device shots the stylet 221 (only its tip can be seen) and the cannula 222 together to the patient's body, more specifically to within the patient's bone 600. More specifically, the cannula 222 which encases the stylet 221 is pushed by the stylet into the patient's body, specifically to within the bone 600.

FIG. 17e shows the device, after separating the main body of device 1 from the setting assembly 400. By this separation, the setting assembly 400 supports the stylet 221 and cannula 222 in a stable configuration, attached to the patient's body 500.

FIG. 17f shows the removal of the stylet 221 from within cannula 222. As previously noted, the sharp stylet 221 is used for providing a penetration power that pushes the cannula 222 to within bone 600. After completion of the penetration, the stylet 221 is no longer necessary, as the channel to within the bone is already provided via cannula 222. Therefore stylet 221 is removed from within the cannula 222. Next, by means of a syringe, or another medical device, fluid can be provided to within bone 600, via cannula 222, or a sample from the bone 600 can be obtained through cannula 222.

As shown, the device of the invention provides a channel for fluids to within the bone 600. The device is very safe, as it comprises two safety measures that eliminate unintentional, accidental, or erroneous activation, or wrong operation. The device of the invention can be activated only when it is unlocked, is in contact with the patient's body and a force is applied on the device against the patient's body. Furthermore, the shot is possible only towards the patient's body, and a shot in and opposite direction (i.e., away from the patient's body or towards the operator of the device) is impossible. All these features are very important to ensure a reliable and safe operation.

The activator assembly 100 will now be described in more detail, with reference to FIGS. 3, 4, and 5. First tube 113 has holes 117a and 117b, having a diameter slightly larger than of balls 116a and 116b. Tube 113 also has two opposite stairs 120a and 120b. Each stair 120 has a front wall 121 for locking tube 113 within trigger 112, and two side walls 123 for guiding tube 113 within corresponding channels 140a and 140b within trigger 112 (best seen in FIGS. 22 and 23), thereby enabling it to perform only a guided linear movement within trigger 112. First tube 113 also comprises two opposite first openings 132a and 132b (not shown) for joining between the first tube 113 of the activator assembly 100 and the second tube 331 of the barrel assembly 300. In other words, the openings enable joining of the activator assembly 100 and the barrel assembly 300 in a manner that will be elaborated hereinafter. First tube 113 further comprises an external groove 133 that typically spans 90° of the periphery of first tube 113. Said external groove 133 comprises two recesses (not shown) that are located 90° respectively at the two ends of groove 133. Said two recesses are used for positioning the safety catch 111 in the "locked" and "unlocked" states of the device 1, respectively.

Figure 22:
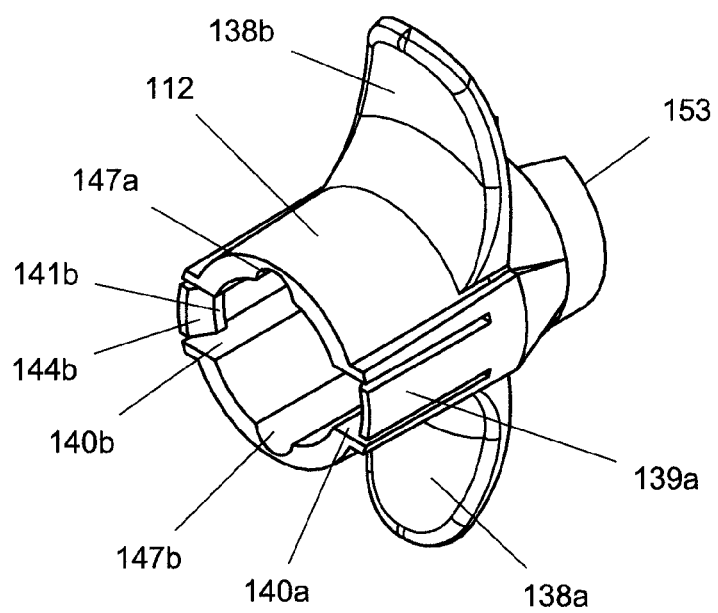
FIG. 22 shows a front view of the trigger of the device.
Figure 23:
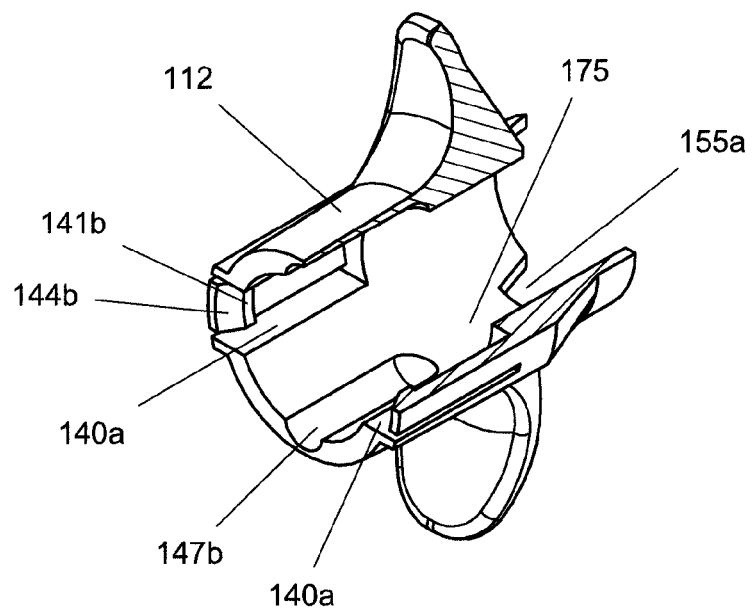
FIG. 23 is a three quarter cross section of the trigger of the device.
Figure 24:
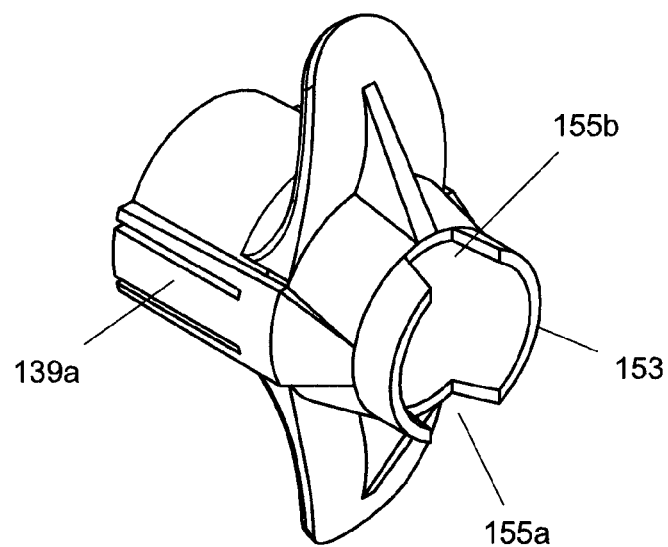
FIG. 24 is a rear view of the trigger of the device.

Trigger 112 has two wings 138a and 138b, for enabling pulling the trigger only in one direction (away from the patient's body). Trigger 112 further comprises the two channels 140a and 140b, for enabling first tube 113 a limited guided linear movement within trigger 112. Two first snaps 139a and 139b (best seen in FIGS. 22 and 24) are provided at the two channels 140a and 140b respectively. Each of said first snaps comprises a hook 141a, 141b which engages respectively the front wall 121a, 121b of the first tube 113, preventing trigger 112 from moving to a proximal direction relative to tube 113. Hereinafter, the proximal direction is defined as the direction towards the operator of the device (i.e., to the direction of the safety catch 111, and away from the patient's body), while the distal direction is defined as the direction towards the patient's body (i.e., away from the operator and in a direction toward the tuning element 441). The two hooks 141 are slightly slanted 144a, 144b towards the distal direction as best shown in FIG. 22. Trigger 112 further comprises two opposite round longitudinal grooves 147a and 147b. It should be noted, however, that the longitudinal grooves 147 do not span the whole length of trigger 112, but they end somewhat before the proximal end 153 of trigger 112 (best seen in FIG. 23). The potion of trigger 112 where there is no groove will be referred herein as the smooth surface 175. Trigger 112 further comprises two opposite second openings 155a and 155b (seen in FIGS. 6a, 23, and 24). The two second openings 155 enable pulling the trigger 112 to the proximal direction relative to first tube 113, during the unlock state of the safety catch 111. On the other hand, such movement is prevented during the locked state of the safety catch 111.

The safety catch 111 comprises two opposite indexing snaps 156a and 156b (shown in FIGS. 3, 6a and 6b), at least one of them comprises an indexing protrusion 157. Said indexing protrusion 157 slides along external groove 133 of the first tube 113 upon turning of the safety catch 111, and is designed to rest within one of its recesses at the "locked" and "unlocked" states respectively.

Figure 3:
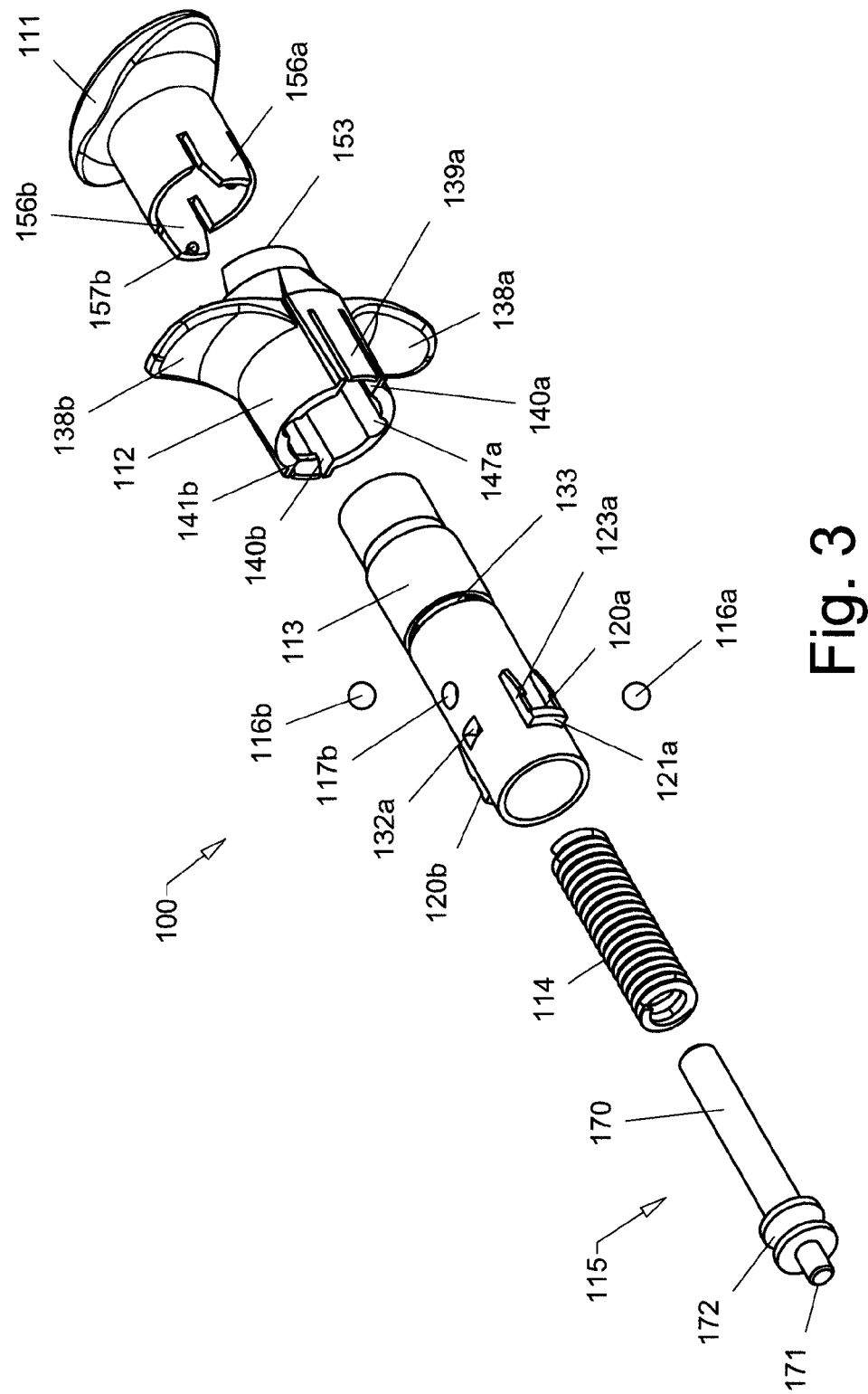
FIG. 3 is an exploded isometric view of the activator assembly.

With reference to FIG. 3, hammer 115 has a proximal portion 170 which enters the main spring 114, and a distal pin 171 for hitting the stylet 221 upon activation of the device. The hammer further comprises a peripheral round groove 172, for accepting balls 116a and 116b during the loaded state of the device. However, upon activation of the device, the balls 116 are released from within said groove 172.

Figure 4:
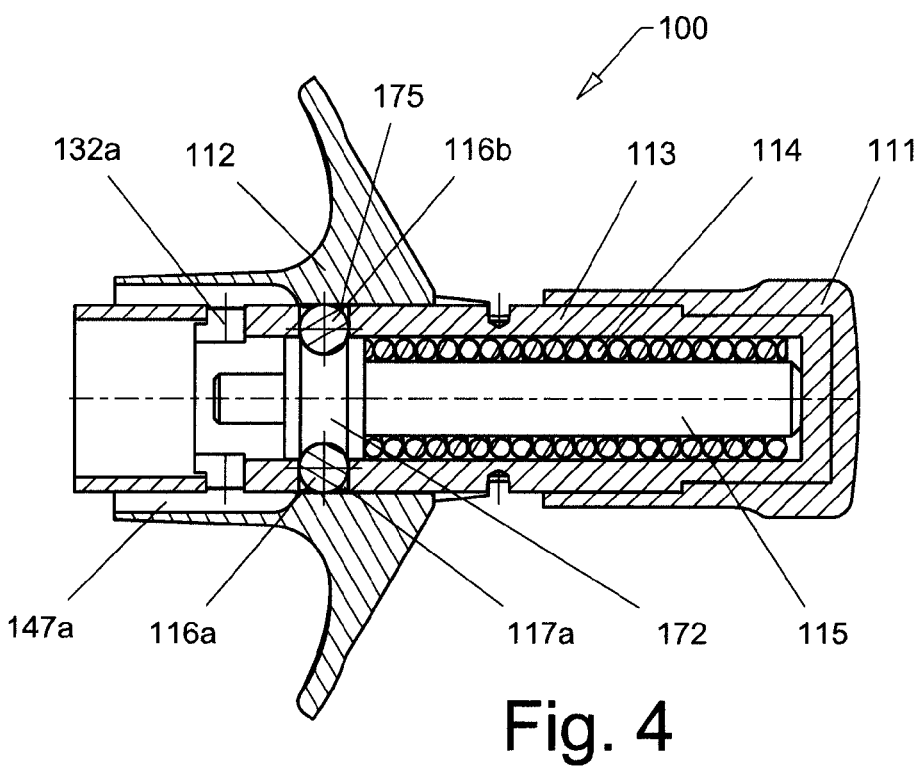
FIG. 4 is a cross-sectional view of the activator assembly.
Figure 5:
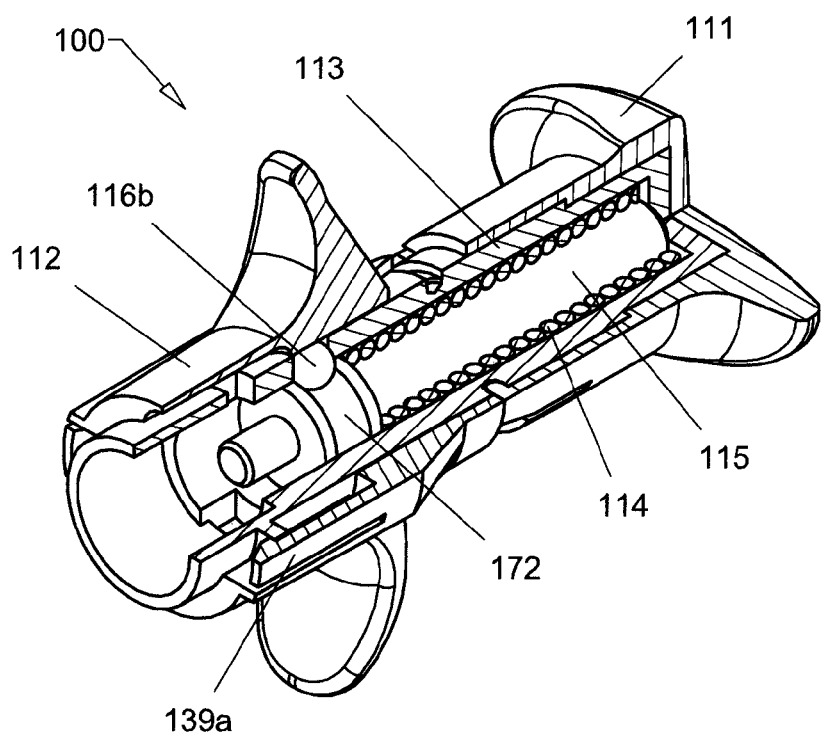
FIG. 5 is a three quarter cross-sectional view of the activator assembly in its cocked configuration.
Figure 6A:
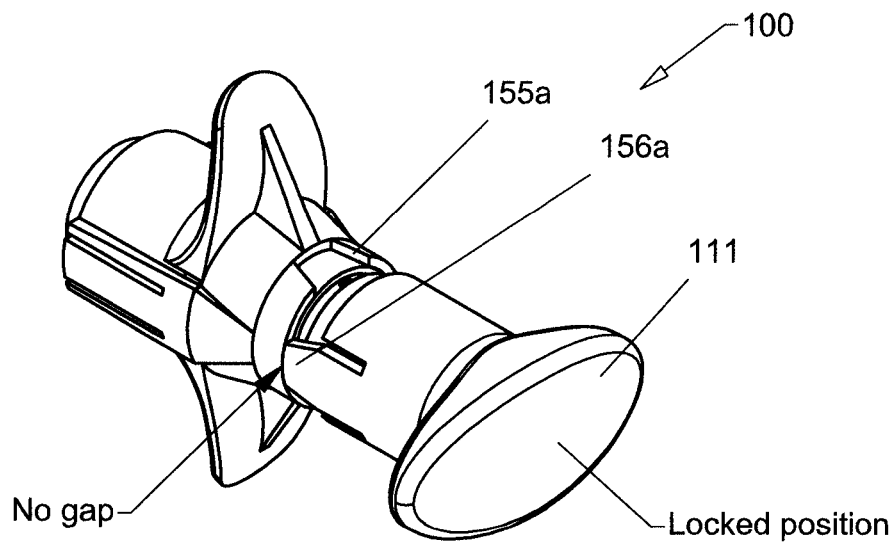
FIG. 6a shows the safety catch of the device in its locked position.
Figure 6B:
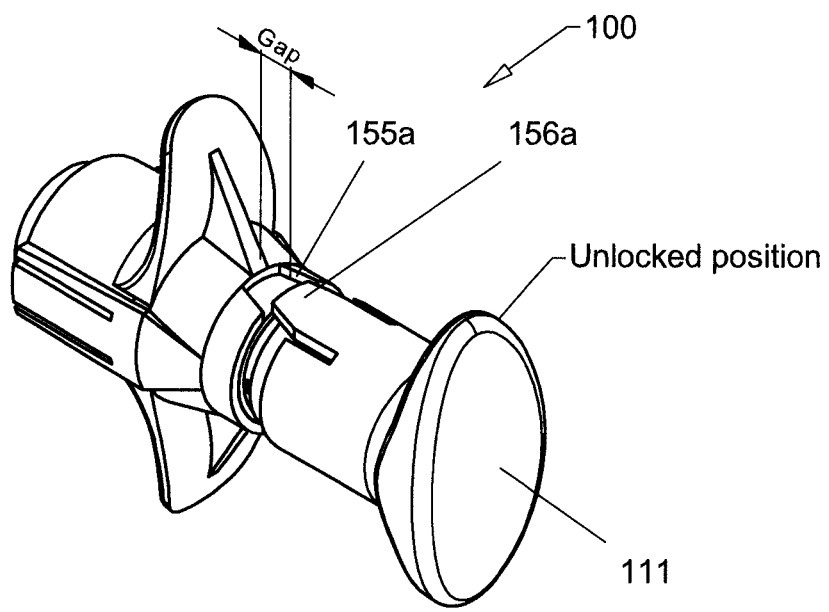
FIG. 6b shows the safety catch of the device in its unlocked position.
Figure 15:
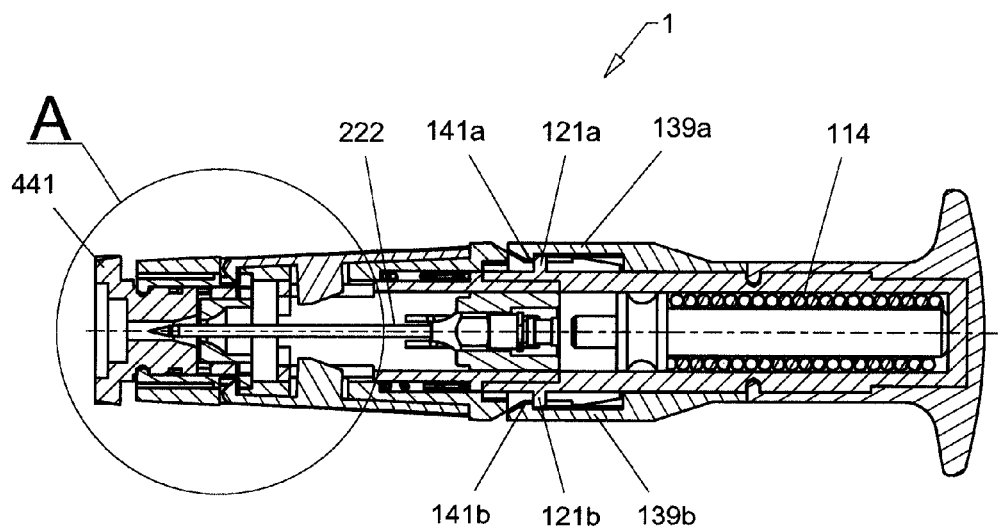
FIG. 15 is a cross sectional top view of the device of the invention in its cocked state.
Figure 16:
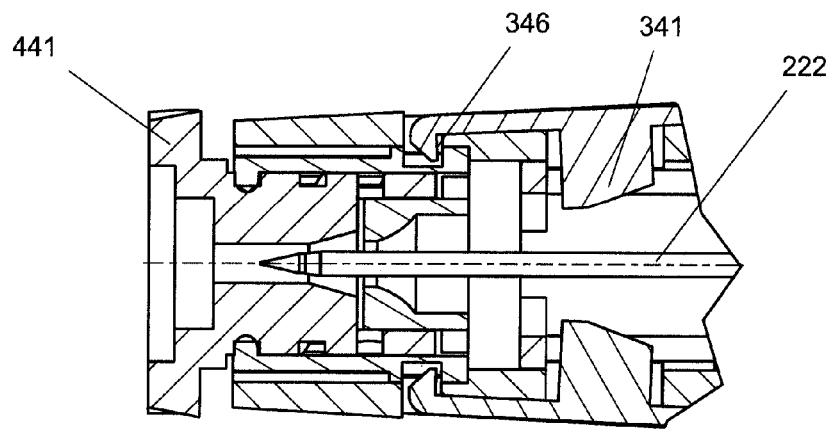
FIG. 16 is a detail view of A of FIG. 15.

FIGS. 4 and 5 show the activator assembly in its loaded state. The main spring 114 is compressed, balls 116a and 116b are pressed by the smooth portion 175 of trigger 112 and through holes 117a and 117b toward groove 172 of the hammer, thereby locking the hammer 115, and preventing it from moving to the distal direction. Furthermore, snaps 139a and 139b of trigger 112 lock the first tube 113 within the trigger 112, preventing trigger 112 from moving to the proximal direction (as shown in FIGS. 3 and 15). Finally, in this state the safety catch is positioned in its locked state.

The barrel assembly 300 is shown in FIGS. 7, 8, and 9. Second tube 331 has second snaps 335a and 335b, for joining the barrel assembly 300 to activator assembly 100. Furthermore, the second tube further comprises two opposite stoppers 336a and 336b, used for preventing the release of the needle assembly 200 from the device 1 during its cocked state. The second tube further comprises two opposite rectangular windows 337a and 337b, whose length is larger than the length of corresponding windows in barrel jacket 333. Finally, the second tube 331 comprises a step 341 for pressing against the secondary spring 332.

The secondary spring 332 and second tube 331 are inserted to within barrel jacket 333. The barrel jacket 333 has two opposite windows 340a and 340b, through which two opposite beveled cams 344a and 344b of elastic latches 334a and 334b respectively are entered. The cams maintain the barrel jacket 333 and the second tube 331 together, while letting the second tube 331 to make some limited longitudinal movement within barrel jacket 333, in view of the difference of length between windows 337 and 340. The spring 332 therefore causes a gap 160 (see FIG. 17b), which is eliminated when the device is pressed against the patient's body 500. The size of the gap is essentially the difference between the lengths of windows 337 and 340. Barrel jacket 333 has still additional two opposite windows 345a and 345b, through which two respective hooks 346a and 346b enter. These hooks hold the setting assembly 400 within the device 1, specifically the second holder 442 during the cocked state. Barrel jacket 333 also comprises at its proximal end two opposite beveled fingers 349a and 349b, for opening snaps 139a and 139b of the trigger upon pressing the device against the patient's body, and elimination of the gap 160. Only the elimination of the gap and opening of the snaps 139 enable pulling the trigger 112 to activate the device (or in other words, release of the second safety measure mentioned before). Moreover, the device is preferably designed to allow closure of the gap and activation of the device only when essentially all the distal surface of the setting assembly comes in contact with the patient's body, and in such a manner this ensure activation of the device only when positioned essentially perpendicular to the bone surface.

The setting assembly 400 will now be described, with reference to FIGS. 10 and 11. The tuning element 441 has an external helical channel 443, enabling the definition of the trocar needle penetration depth, according to the angular position of the tuning element. More specifically, the helical portion is entered to within second holder 442, in such a manner that the snaps 444a and 444b engage the helical channel 443. More specifically, one or more fingers 445 of snaps 444 engage the channel 443. Optionally, two or more recesses within the channel are provided to enable seating of the one or more fingers within the channel in predefined positions respectively, each of such positions defines one specific penetration depth. The second holder 442 also has two opposite recesses 446a and 446b, to engage with the barrel assembly 300, by means of hooks 346a and 346b of elastic latches 334a and 334b. It should be noted, however, that the adjustment of he penetration depth by the setting assembly is optional. The setting assembly may be provided in a fixed pre-adjusted penetration depth, while further adjustment is not allowed.

The activation of the device will now be described. The various operation stages of the device are illustrated in FIGS. 17a-17f. The body of the patient is indicated by numeral 500. The initial stage of the device is shown in FIGS. 17a, 14, 15, and 16. In the initial stage, the device 1 is cocked and locked. More specifically, the cocked configuration is provided when the needle assembly 200 is fully positioned within the device 1, and the main spring 114 of the activator assembly 100 is loaded. During the locked configuration, the safety catch 111 is in its "locked" position (see also FIG. 6a). Moreover, a gap 160 exists between trigger 112 and barrel jacket 333. The gap provides a second safety means, as the device cannot be activated as long as this gap exists, even when safety catch 111 is turned into its "unlock" state (best shown in FIG. 6b).

Before the use of the device, the penetration depth may be tuned by means of tuning element 441. The tuning selects between several penetration depths, and is performed by turning the turning element 441 to a selected angular position.

FIG. 17b shows the device in its unlocked state as provided by turning the safety catch 111 (first safety means) into its unlocked position (i.e., turning it 90° from its initial locked position). The device 1 is in contact with the patient's body 500, however, it is still inoperable, as the gap 160 still exists.

FIG. 17c shows the state of the device 1 just before its activation. More specifically, the second safety means is neutralized by the user applying a linear distal direction force 161 on the safety catch 111 directed to the patient's body 500, thereby eliminating gap 160. The elimination of the gap opens the snaps 139a and 139b, thereby uncoupling them from first tube 113. This enables activation of the device by pulling trigger 112 to the proximal direction.

FIG. 17d shows the device 1 just after its activation. As mentioned, the activation is provided by pulling trigger 112 in a proximal direction 167 away from patient's body 500. The activation of the device cause the balls 116a and 116b to release hammer 115, which is in turn pushed by the previously loaded main spring 114 in the distal direction. Hammer 115 hits the stylet 221, which in turn also pushes the cannula 222 in the distal direction. The stylet 221 and cannula 222 leave the first holder 223, and settle in second holder 442. The hammer 115 simultaneously hits the first holder 223, pushing it also in the distal direction. The first holder 223 in turn hits the beveled cams 344 causing uncoupling of the setting assembly 400 from barrel assembly 300. Following the process above, the stylet 221 and cannula 222 together penetrate the patient's body, more specifically to within the patient's bone 600.

FIG. 17e shows the device, after separating the main body of the device 1 from the setting assembly 400. By this separation, the setting assembly 400 supports the stylet 221 and cannula 222 in a stable configuration, attached to the patient's body 500.

FIG. 17f shows the removal of the stylet 221 from within cannula 222. As previously noted, the sharp stylet 221 is used for providing a penetration power that pushes the cannula 222 to within bone 600. After completion of the penetration, the stylet 221 is no longer necessary, as the channel to within the bone is already provided via cannula 222. Therefore stylet 221 is removed from within the cannula 222. Next, by means of a syringe, or another medical device, fluid can be provided to within bone 600, via cannula 222, or a sample from the bone 600 can be obtained through cannula 222.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

The invention claimed is:

1. A device for the insertion of a cannula into a bone of a patient, which comprises:
   a. an activator assembly for activating the device;
   b. a needle assembly which comprises a stylet and cannula;
   c. a barrel assembly for containing said stylet and cannula in a loaded state prior to the device activation; and
   d. a setting assembly for adjusting a penetration depth of said cannula into the patient's bone;

wherein:
   e. said activator assembly comprises a first safety mechanism in a form of a safety catch that prevents activation of the device unless said safety catch is released;
   f. said activator assembly comprises a trigger that triggers activation of the device only if pulled toward a proximal direction, while pulling to a distal direction is prevented, thereby eliminating reverse direction activation;
   g. the device comprises a second safety mechanism that prevents activation of the device by locking it unless said setting assembly is pushed against a patient's body, thereby causing closure of a gap in the device between a jacket which is located in said barrel assembly and said activator assembly, hence the device becomes ready for activation only when placed properly against the patient's body.

2. A device according to claim 1, wherein said gap between said barrel assembly and said activator assembly is formed by means of a secondary spring which is located between said two assemblies.

3. A device according to claim 1, wherein when the device is pushed against the patient's body, but released without triggering, the gap is recreated, and the device becomes locked again.

4. A device according to claim 1, wherein said needle assembly is maintained in a loaded state within the device by means of a loaded main spring.

5. A device according to claim 1, wherein said setting assembly automatically separates from a main body of the device together with said needle assembly after activation of the device, and said setting assembly remains on the patient's body to support, stabilize, fix and maintain the cannula in place.

6. A device according to claim 1, wherein the stylet is removed from the cannula after activation of the device, leaving the cannula penetrated within the bone, thereby producing a channel from the exterior of the patient's body to within the medullary cavity of the bone.

7. A device according to claim 1, wherein said first safety mechanism is released by means of rotating said first safety mechanism relative to the rest of the device.

8. A device according to claim 1, wherein said stylet is maintained within said cannula, before activation of the device.

9. A device according to claim 1, wherein said setting assembly comprises a turning element with a thread, which defines the penetration depth by means of rotation.

10. A device according to claim 1, wherein said needle assembly is pushed toward the bone upon activation of the device by means of a hammer.

11. A device according to claim 1, wherein said needle assembly further comprises a first holder, said first holder releases the stylet and cannula after the triggering of the device.

12. A device according to claim 11, wherein said first holder automatically releases the setting assembly after the triggering of the device and insertion of said stylet and cannula into the bone.

13. A device according to claim 1, wherein said needle assembly comprises a needle holder that holds the needle aligned in place during the loaded state of the device.

14. A device according to claim 1, wherein said second safety mechanism allows activation of the device only when positioned essentially perpendicular to a bone surface.

15. A device according to claim 1, wherein the setting assembly is pre-adjusted to a fixed penetration depth.

* * * * *